United States Patent
Weston et al.

(10) Patent No.: US 6,716,176 B1
(45) Date of Patent: Apr. 6, 2004

(54) DEVICE FOR USE IN TEMPORARY INSERTION OF A SENSOR WITHIN A PATIENT'S BODY

(75) Inventors: David Edward Weston, Rockford, MI (US); Fredrick Alan Shorey, East Grand Rapids, MI (US); Brian Randall Mulder, Rockford, MI (US)

(73) Assignee: TOBO, LLC, Portland, OR (US)

( * ) Notice: Subject to any disclaimer, the term of this patent is extended or adjusted under 35 U.S.C. 154(b) by 0 days.

(21) Appl. No.: 10/262,226

(22) Filed: Sep. 30, 2002

(51) Int. Cl.[7] ................................................. A61B 8/14
(52) U.S. Cl. ....................................................... 600/462
(58) Field of Search ................................. 600/407–471; 604/22, 27, 28; 128/916; 601/2–4

(56) References Cited

U.S. PATENT DOCUMENTS

| | | | |
|---|---|---|---|
| 4,100,309 A | 7/1978 | Micklus et al. ................. 427/2 |
| 4,407,294 A | 10/1983 | Vilkomerson ............... 128/660 |
| 4,408,612 A | 10/1983 | Utsugi ........................ 128/660 |
| 4,428,379 A | 1/1984 | Robbins et al. ............. 128/660 |
| 4,431,006 A | 2/1984 | Trimmer et al. ............ 128/660 |
| 4,671,295 A | 6/1987 | Abrams et al. ............. 128/663 |
| 4,722,347 A | 2/1988 | Abrams et al. ............. 128/663 |
| 4,886,059 A | 12/1989 | Weber ................... 128/207.15 |
| 4,947,854 A | 8/1990 | Rabinovitz et al. ..... 128/662.04 |
| 5,048,524 A | 9/1991 | Bailey ........................ 128/634 |
| 5,095,910 A | 3/1992 | Powers .................. 128/662.05 |
| 5,127,407 A | 7/1992 | Tan ............................ 128/633 |
| 5,205,292 A | 4/1993 | Czar et al. ............. 128/662.03 |
| 5,228,440 A | 7/1993 | Chung et al. ............... 128/633 |
| 5,265,612 A | 11/1993 | Sarvazyan et al. ..... 128/660.01 |
| 5,284,146 A | 2/1994 | Czar et al. ............. 128/662.03 |
| 5,291,896 A | 3/1994 | Fonger et al. ............... 128/713 |
| 5,304,214 A | 4/1994 | DeFord et al. .............. 607/105 |
| 5,315,995 A | 5/1994 | Rivers ........................ 129/634 |
| 5,331,947 A | 7/1994 | Shturman ....................... 126/4 |
| 5,335,663 A | 8/1994 | Oakley et al. .............. 128/662 |
| 5,443,445 A | 8/1995 | Peters et al. .................. 604/27 |
| 5,531,714 A | 7/1996 | Dahn et al. ................. 604/264 |
| 5,673,694 A | 10/1997 | Rivers ........................ 128/634 |
| 5,743,260 A | 4/1998 | Chung et al. ............... 128/633 |
| 5,743,261 A | 4/1998 | Mainiero et al. ........... 128/633 |
| 5,775,328 A | 7/1998 | Lowe et al. ............. 128/662.06 |
| 6,106,475 A | 8/2000 | Lowe et al. ................ 600/462 |
| 6,231,514 B1 | 5/2001 | Lowe et al. ................ 600/462 |

FOREIGN PATENT DOCUMENTS

| | | |
|---|---|---|
| EP | 0 246 176 A2 | 11/1987 |
| GB | 2268074 | 1/1994 |
| WO | WO 93/03668 | 3/1993 |
| WO | WO 97/49337 | 12/1997 |
| WO | WO 99/48424 | 9/1999 |

*Primary Examiner*—Ali M Imam
(74) *Attorney, Agent, or Firm*—Chernoff, Vilhauer, McClung & Stenzel, LLP

(57) ABSTRACT

A device for use in placing a non-sterile sensor probe such as an ultrasound scanning transducer in a desired position within a patient. A flexible probe-receiving tube has a closed distal end so that a probe inserted within the tube through an open end located outside the patient is isolated from contact with the interior of the patient's body. The probe-receiving tube is attached to and extends alongside a chest drain tube which supports the probe-receiving tube in a location proximate an organ to be observed. An attached sterile sensor may be attached directly to an interior blood vessel, and sensors such as an ultrasonic sensor, a light emitting sensor, or a multi-function combination sensor may be used in the probe-receiving tube.

17 Claims, 4 Drawing Sheets

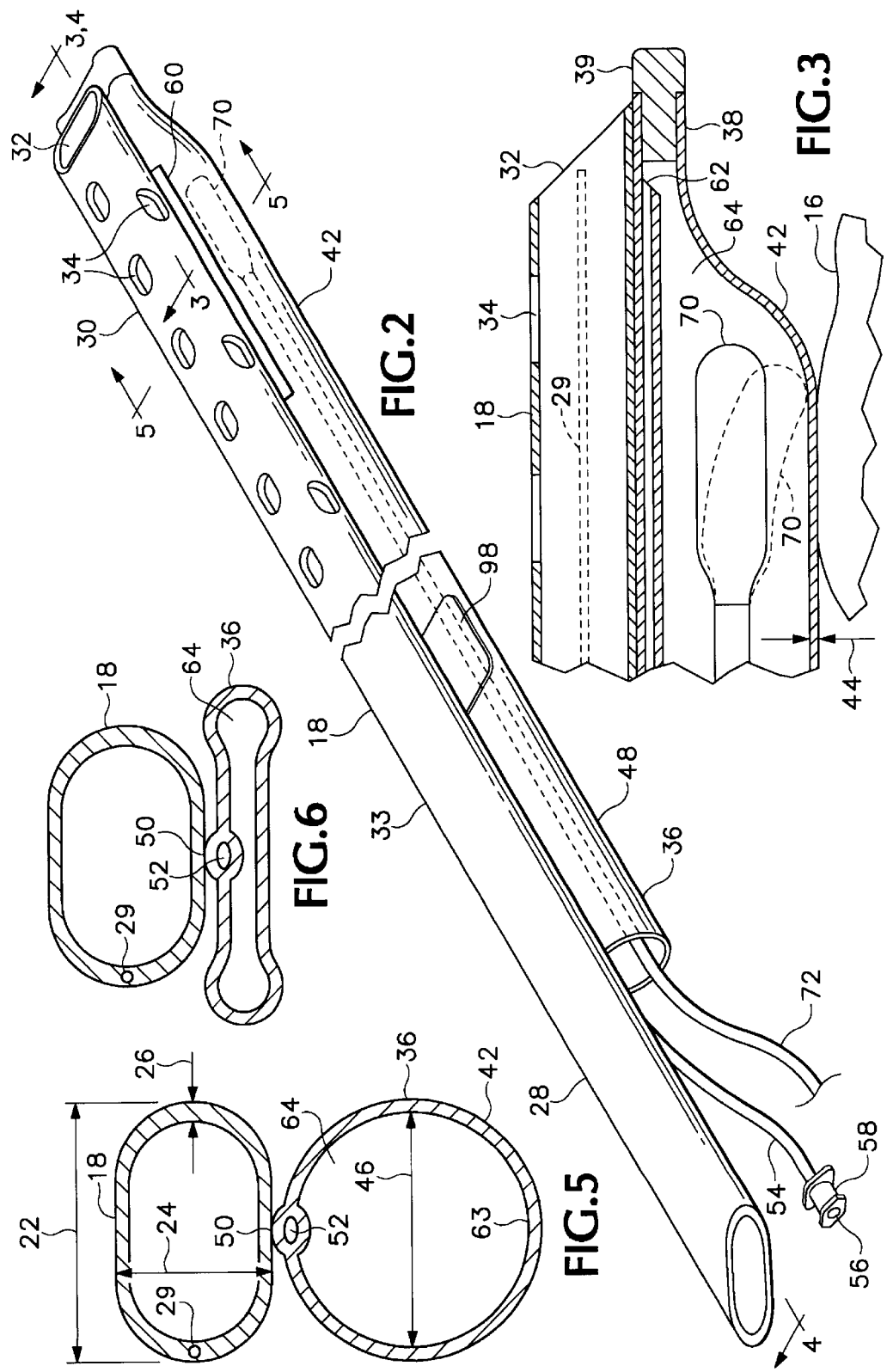

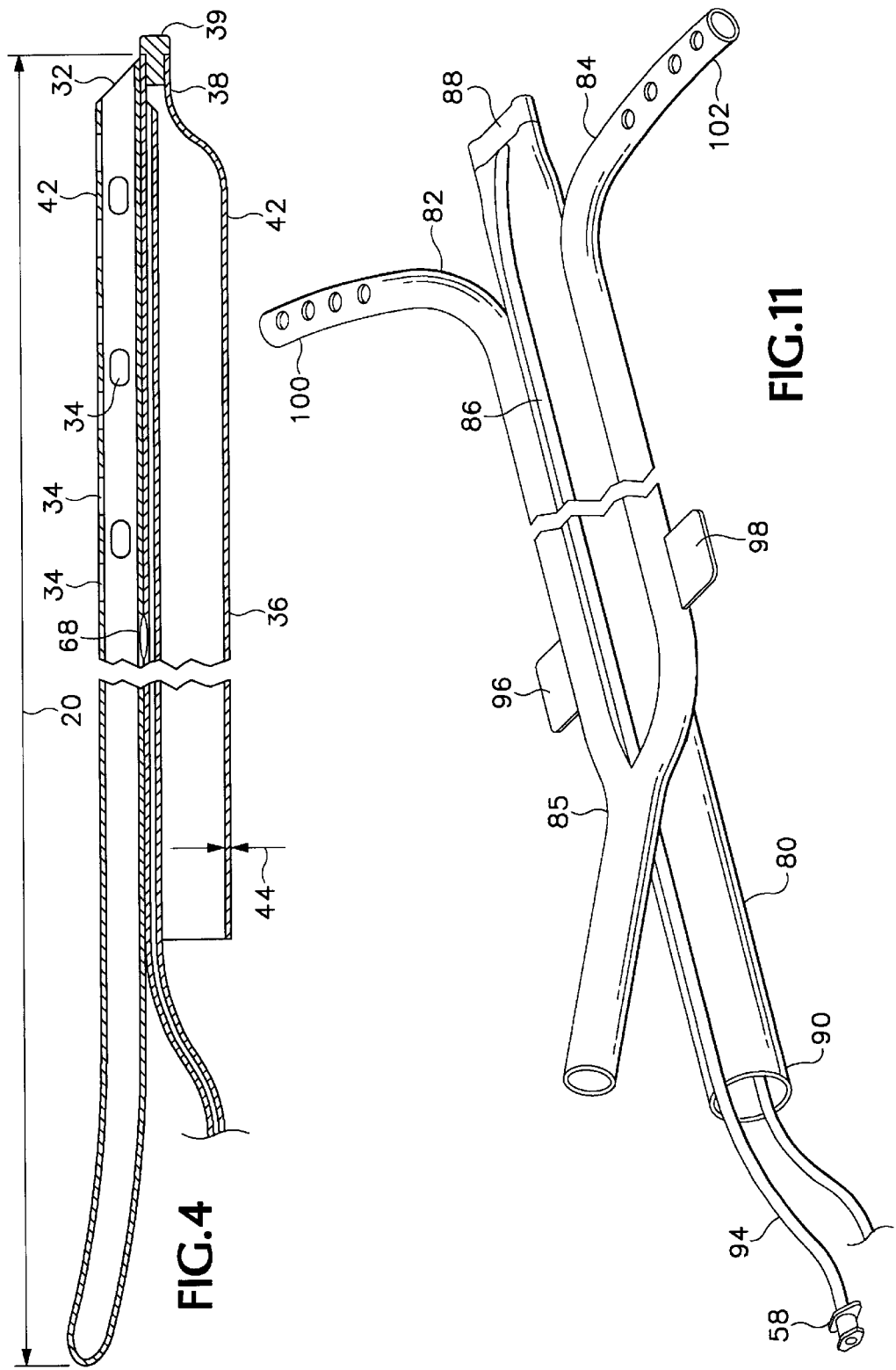

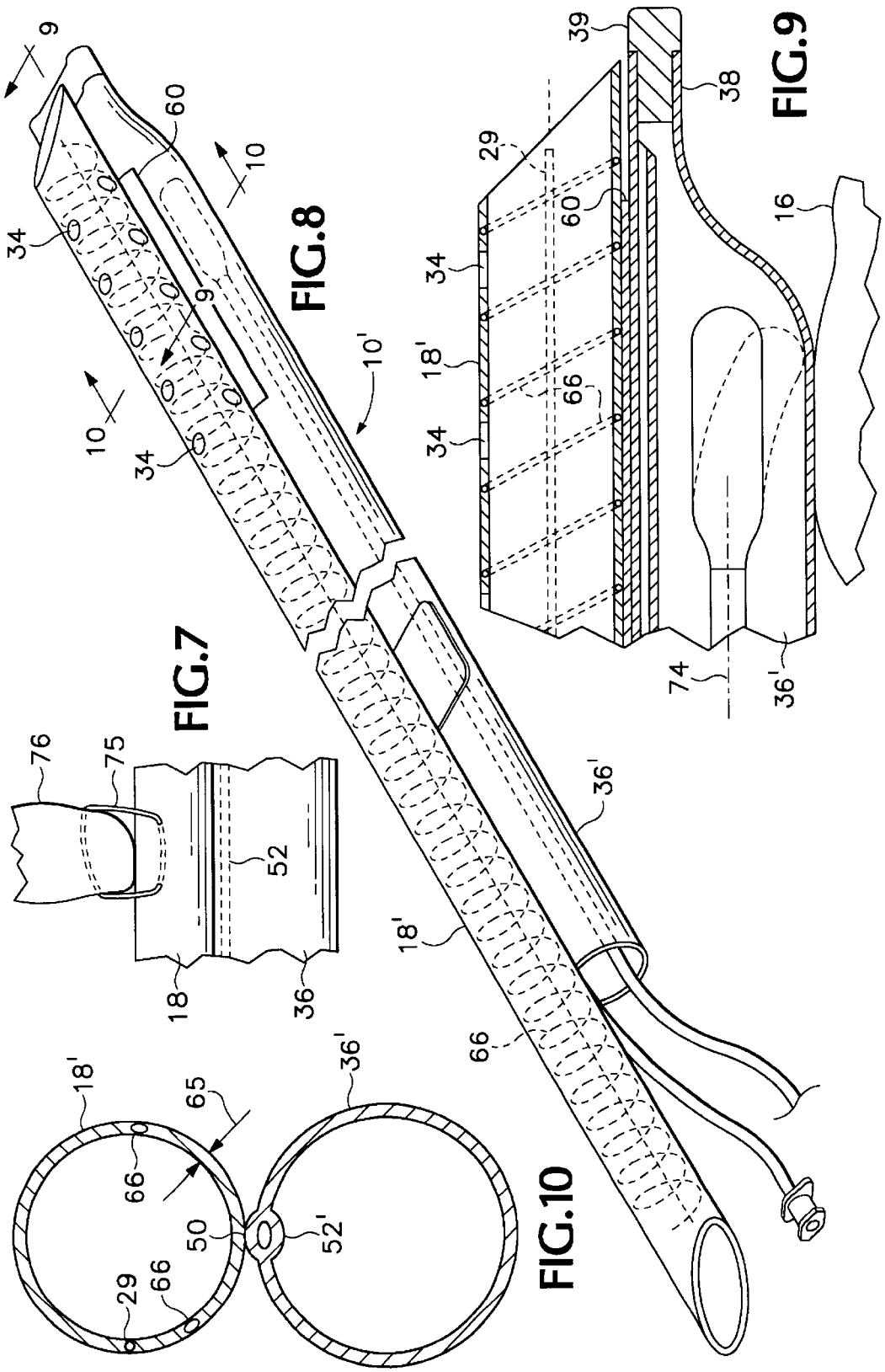

DEVICE FOR USE IN TEMPORARY INSERTION OF A SENSOR WITHIN A PATIENT'S BODY

BACKGROUND AND SUMMARY OF THE INVENTION

The present invention relates to placement of sensors within a patient's body, and in particular relates to facilitating repeated placement of a non-sterile sensor, such as an ultrasound transducer, precisely into a required location in a patient's body in a minimally invasive and sterile manner.

It is frequently desirable to obtain information regarding the size, shape, and function of internal body organs by the use of ultrasound echo imaging. For example, it is desirable to evaluate the performance of a patient's heart after cardiac surgery. In the time immediately after such surgery, patients frequently have significant cardiac functional problems, and visualization and examination of the heart by ultrasound echo imaging may be of critical value.

Devices for use in placing and holding sensor probes such as ultrasound sensors are disclosed, for example, in Lowe, et al. U.S. Pat. Nos. 5,775,328 and 6,231,514.

In accordance with the present invention a probe-receiving device includes collapsible probe-receiving tube that is supported by an elongate support member that is attached to and extends along at least a portion of the probe-receiving tube. A proximal portion of the probe-receiving tube is available outside the patient's body as an entrance through which to insert a non-sterile probe into the interior of the patient's body. A distal portion of the elongate support member is able to be manually formed into and remain in a desired configuration, and thus may be useful to control the location of the probe enclosed within the probe-receiving tube attached to it.

In a probe-receiving device which is one embodiment of the invention the elongate support member is in the form of a chest drain tube placed within the thoracic cavity of a cardiac surgery patient prior to closing the patient's chest, with the proximal portion of the device being located externally of the patient's abdomen and the distal portion of the device extending through an opening in the abdominal wall and thence toward the patient's heart, so that the probe-receiving tube is available in a desired position during the period following cardiac surgery when it is critical to evaluate the function of the heart.

In one preferred embodiment of the invention the elongate support member has the form of a drain tube having a thin wall containing an embedded supporting member. In one preferred embodiment of the invention such an embedded supporting member may be a wire in the form of a helical coil embedded in and extending along the drain tube wall to define and support its open tubular configuration.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 2 is a perspective view of a combined chest drain tube and probe-receiving tube according to the present invention.

FIG. 3 is a sectional view of part of a distal end portion of the combined chest drain tube and probe-receiving tube shown in FIG. 2.

FIG. 4 is a sectional side elevational view of the combined chest drain tube and probe-receiving tube shown in FIGS. 1–3, taken on line 4—4 of FIG. 2.

FIG. 5 is a sectional view, taken along line 5—5 of FIG. 2.

FIG. 6 is a sectional view taken along line 5—5 of FIG. 2, with the distal end portion of the probe-receiving tube in a collapsed condition.

FIG. 7 is a simplified view showing a short portion of the combined drain tube and probe-receiving tube shown in FIG. 1, showing a suture holding the distal end portion of the device in its required location inside a patient.

FIG. 8 is an isometric view of a combined chest drain tube and probe-receiving tube which is another embodiment of the present invention.

FIG. 9 is a sectional view of a part of a distal end portion of the combined chest drain tube and probe-receiving tube shown in FIG. 8.

FIG. 10 is a sectional view of the probe-receiving tube, taken along line 10—10 of FIG. 8.

FIG. 11 is an isometric view of a portion of a probe-receiving tube and associated drain tubes, in another alternative embodiment of the device.

DETAILED DESCRIPTION OF THE PREFERRED EMBODIMENT

Figure 1:
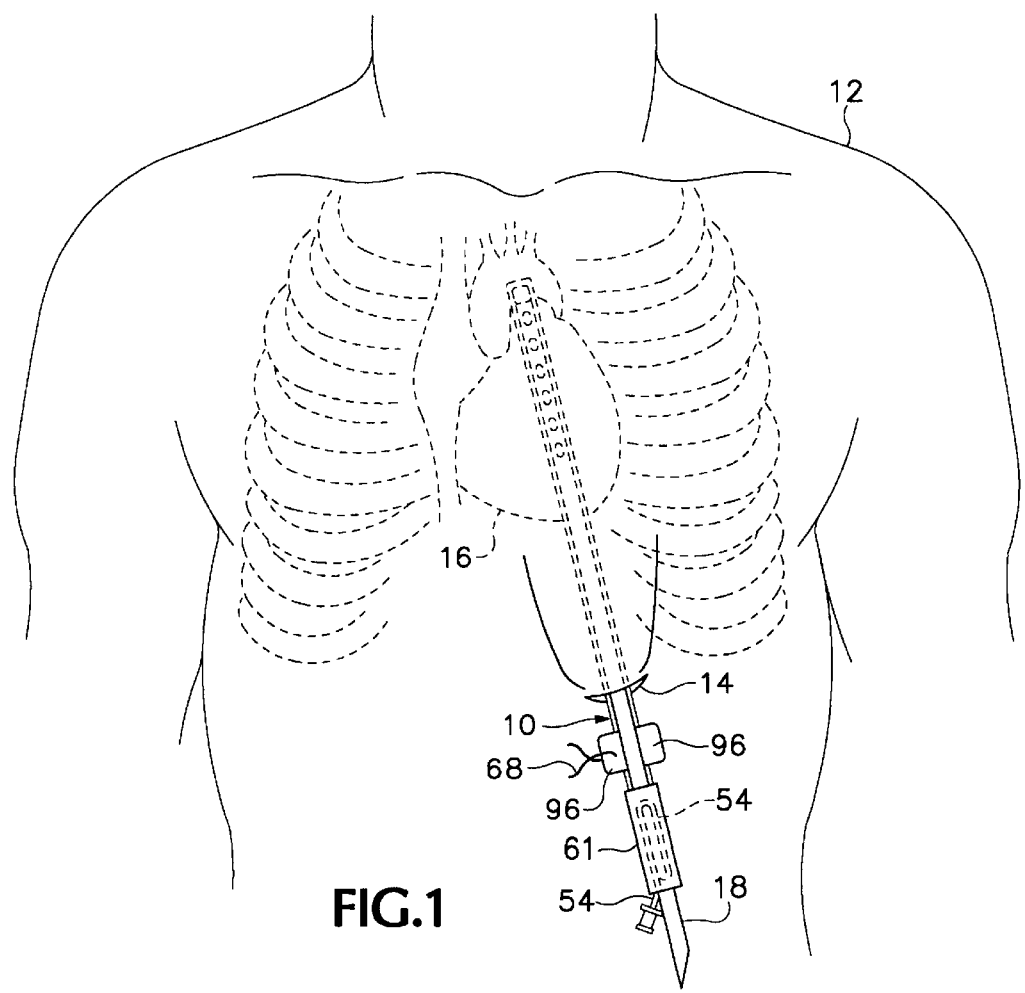
FIG. 1 is a simplified view of a patient's torso, showing a device embodying the present invention in place.

Referring now to the drawings which form a part of the disclosure herein, a device 10 embodying the present invention is shown in place in a cardiac surgery patient 12, with the device 10 extending into the interior of the thoracic cavity of the patient 12 through a surgical opening 14 below the sternum, so that a sensor can later be positioned within the device 10 in a desired location within the thoracic cavity of the patient, in order to obtain, for example, an ultrasound image of the patient's heart 16.

As shown in greater detail in FIGS. 2, 3, and 4, the device 10 includes a chest drain tube 18, of a resiliently flexible silicone rubber material which is clear and translucent and suitable for biomedical applications. One satisfactory material for the drain tube 18 has, for example, a Shore A hardness of 60±5 durometer, at least 1100 psi tensile strength, at least 600% elongation, and tear-resistance of at least 130 pounds per inch. These characteristics are not critical, but what is necessary is for the drain tube 18 to be suitable for biomedical use and to be somewhat flexible. The chest drain tube 18 shown herein as an example has a length 20 of about 445 mm and is oval in cross-section, having a width 22 of about 1.8 cm and a height 24 of about 9 mm, but these dimensions are not critical to the present invention. A maximum wall thickness 26, at one end of the oval cross-section shape, may be about 2–5 mm.

A longitudinally extending wire 29 is embedded in the wall of the drain tube. The wire 29 is of malleable metal, heavy enough to retain a desired adjusted configuration such as an angular diversion from the normal axis of the drain tube once bent, as shown in broken line in FIG. 1, for example, so that the drain tube 18 will support a sensor probe in a desired location within a patient. The drain tube can thus be bent so that its distal end portion diverges by a desired angle from its original axial orientation.

A proximal portion 28 of the chest drain tube 18 normally remains outside the body of a patient 12, while the drain tube 18 extends through the surgical opening 14 with its distal end portion 30 in position in the pericardial space to remove blood following open heart surgery. The blood can enter into the lumen of the chest drain tube through the open distal end 32 and several openings 34 defined through the wall of the distal end portion 30.

Extending along and attached to the distal end portion 30 and an intermediate part 33 of the drain tube 18 is a probe-receiving tube 36, for which the chest drain tube 18 acts as an elongate support member. The probe-receiving tube 36 is of a biologically compatible and ultrasound translucent material such as a silicone rubber similar to that of the chest drain tube 18, in a preferred embodiment of the invention. In an alternative preferred embodiment of the device 10, a probe-receiving tube 36 might be made of any material translucent with respect to a relevant frequency of light to allow the use of light emitting sensors. In yet another separate preferred embodiment of the invention, a probe-receiving tube may be made of any material permeable to both sound and light to allow the use of sound and/or light emitting sensors. Such materials should not absorb or reflect the relevant frequencies of sound or light, and may include various plastic resins or types of rubber.

The probe-receiving tube 36 has a thin, flexible wall and is generally oval or circular in cross-section when extended, as shown in FIGS. 1–5. It has a closed distal end 38 which may be closed by a plug 39 fixed in place by a suitable adhesive. The probe-receiving tube 36 has a wall thickness 44 of about 0.76 mm and an inside diameter 46 of about 16 mm (48 French) to permit it to receive an available sensor probe such as an ultrasound probe used in transesophageal examination. The size of the interior space 64 defined within the probe-receiving tube 36 is thus ample to admit an ultrasound probe 70 of the size and type well known for use transesophageally in adults, such as probes including a piezoelectric transducer available from Hewlett-Packard, Advanced Technology Laboratory, or Acuson. For example, a Hewlett-Packard Omni II™ model HP 21367A transducer probe would be satisfactory. A transducer probe 70 of smaller size, such as a Biplane™ pediatric transesophageal probe model HP 21366A or a Multiplane™ pediatric transesophageal probe model HP 21381A, may be utilized if available. The wall thickness 44 is thus small enough that the wall is flexible easily and allows the probe-receiving tube 36 to open to receive a sensor probe or to conform easily to the shape of an object pressing against its outside surface.

The probe-receiving tube 36 extends along and is securely adhered to the chest drain tube 18, in a narrow area 50 extending along the medial portion of the drain tube 18, as shown best in FIGS. 5 and 6. If desired, for use in certain situations the distal portion 42 of the probe receiving tube 36 may be separable from the distal end portion 30 of the drain tube 18 over a zone extending, for example, a distance of 5–15 cm, and preferably about 10–12 cm from the distal end 32 of the drain tube 18, in order to allow some freedom of movement of the transducer 70 while the drain tube 18 is kept in place where required.

A small tubular conduit 52 is defined within and extends along the wall of the probe-receiving tube 36 between the lumen of the probe-receiving tube 36 and the drain tube 18. The conduit 52 communicates with an extension tube 54 extending away from the proximal end 48 of the receiving probe tube 36. The extension tube 54 may be closed off tightly, by a plug 56 fitting in an end coupling 58 fastened to the extension tube 54. At the distal end 32 of the drain tube 18, a short portion of the small conduit 52 is opened, as by skiving, prior to inserting the end plug 39, to form an internal port 62, shown in FIG. 3, communicating with an interior space 64 within the probe-receiving tube 36, so that a fluid can be delivered to the interior space 64 as desired during the use of a sensor probe 70.

As shown in FIG. 1, the extension tube 54 may be folded into the interior of the proximal end 48 of the probe-receiving tube and held in place closely alongside the drain tube 18 by a short sleeve 61 extending around the proximal end 48 of the probe-receiving tube 36, the extension tube 54, and its end coupling 58, to protect them and keep them from dangling into an interfering location prior to the need for their use.

Preferably, at least the interior surface 63 of the probe-receiving tube 36, defining the interior space 64, is coated with a friction-inhibiting material which is preferably hydrophilic and which makes the interior surface very slippery when it is wetted by water or blood. This material resists adhesion and clotting of blood and is also used on the interior and exterior surfaces of the chest drain tube 18. A coating material suitable for this purpose is a polyvinyl-pyrrolidone-polyurethane interpolymer, as disclosed in Creasy et al. U.S. Pat. No. 4,642,267 for example, available from Hydromer, Inc., of Somerville, N.J.

As best seen in FIG. 3, a portion of the distal end portion 42 of the probe-receiving tube 36 may include or be made of a different material significantly less conductive of ultrasound waves, or of another type of signal energy to be used by a sensor to be placed within the probe-receiving tube. Alternatively, a signal-blocking member 60, of a material through which the chosen types of signal energy are not easily transmitted, such as barium sulfate-loaded silicone or an air-filled plastic foam, for example may be included between the distal portion 30 of the drain tube and the distal end portion 40 of the probe-receiving tube 36.

As shown in FIGS. 8, 9, and 10, a probe-receiving device 10' includes a drain tube 18' that is an alternative to the oval tube shown in FIGS. 1–5 and may be constructed as a generally circular cylindrical tube of material having a wall thickness 65 that is thinner than the wall thickness 26 of the drain tube 18, shown in FIGS. 1–7, with the relatively thin material of the wall of the drain tube 18' supported by an embedded supporting member 66 to retain the shape of the drain tube as desired. For example, the wall thickness 65 may be about 2 mm, when the wall is of a resiliently flexible silicon rubber material such as that described above with respect to the chest drain tube 18.

The drain tube 18' may have a diameter 22' of, for example, 18 mm. Preferably a supporting member 66 such as a helical wire is embedded in the wall to prevent the drain tube from collapsing. The wire helix 66 surrounds and extends along the bore or lumen of the drain tube 18' to retain its patency, yet the wire should be soft and malleable enough, at least in the distal end portion 30 of the drain tube, to permit the drain tube to be bent as desired to optimize its position in a patient's body cavity. As in the device 10 described above, a longitudinally extending support wire 29' may also be embedded in the wall of the drain tube alongside the helical support wire 66.

A probe-receiving tube 36' similar to the probe-receiving tube 36 and including a small tubular conduit 52' is attached securely to the drain tube 18' securely, as by an adhesive attachment, as in the device 10.

The longitudinally extending wire 29' may be similar to the wire 29 described above with respect to the device 10 and serves, together with the helical embedded wire 66, to retain the drain tube 18' in a desired, possibly adjusted, configuration to ensure that the probe-receiving tube 36' remains in the desired location and orientation within a patient's body cavity while the proximal portion of the device 10' extends outward from the surgical opening 14 in the patient's body.

As shown in FIG. 11, a probe-receiving tube 80, which is itself constructed similar to the probe-receiving tube 36, has a pair of drain tubes 82 and 84 arranged along opposite sides of the probe-receiving tube 80. A tubular conduit 86, similar to the tubular conduit 52 in the device 10, extends along the probe-receiving tube 80 to a plug 88, similar to the end plug 39, at the distal end of the probe-receiving tube 80. The drain tubes 82 and 84 may be interconnected with each other in a Y-junction 85 leading into a single drain outlet tube near the proximal end 92 of the probe-receiving tube 80. As in the probe-receiving device 10, an extension tube 94 extends from the conduit 86 and may have a fitting to receive a plug or to receive a fluid to be carried to the interior of the distal end portion of the probe-receiving tube 80.

Each of the drain tubes 82 and 84 preferably includes a malleable wire to permit it to be bent into an angular diversion in a desired direction to receive and drain fluids from the interior of a patient's body cavity, while the device 78 remains in place, as shown in broken line in FIG. 11, for example. Attachment tabs 96 and 98 may be provided on the drain tubes 82 and 84 near the junction 85 to receive sutures to hold the device 78 attached to a patient's body in a required location. The drain tubes 82 and 84 may be securely attached along respective sides of the probe-receiving tube 80 over most of the length of the probe-receiving tube 80, but their distal end portions 100, 102 are separate or may be easily separated from the distal end portion 104 of the probe-receiving tube 80 to permit each drain tube to be placed, if required, at a location spaced apart from the location where the probe-receiving tube 84 is to be held.

Referring once more to FIG. 1, the probe-receiving device 10 may be used for a patient whose chest has been opened for cardiac surgery, by inserting the distal end part 30 of the drain tube 18, together with the attached distal end portion 42 of the probe-receiving tube, through the surgical opening 14 and into the pericardial space within the patient 12. One or more sutures 68 through one or both of a pair of tabs 96 or other such securing device are used to fasten the device 10 in place on the exterior of the patient's abdomen, with the distal portion 42 of the probe-receiving tube 36 preferably resting against the right ventricle of the patient's heart 16.

Preferably, the usual placement of the chest drain tube 18, extending into the body cavity of the patient 12 through the left rectus muscle and fascia in an orientation slightly divergent from vertical, brings the probe-receiving tube 36 into contact with the anterior surface of the epicardium of the right ventricle of the patient's heart 16. The position of the probe-receiving device 10 can be adjusted by the surgeon during surgery, before closure of the chest, and a suture 75 may be placed through the wall of the drain tube 18 tissue in the vicinity of the location where it is desired to use the transducer 70, to keep the distal portion of the probe-receiving device 10 in the proper location and to permit repeated insertion and removal of the transducer 70 through the probe-receiving tube 36 so long as the probe-receiving device 10 is left in the patient.

The openings 34 are thus left available, unobstructed, to provide the required drainage of the pericardial space once the patient's chest has been closed in completion of surgery. The probe-receiving tube 36 is thus kept properly located and available to receive a probe such as a steerable ultrasound transducer probe 70, other types of ultrasonic sensors, a light emitting sensor, or a multi-function combination sensor. The appropriate sensor probe 70 can be inserted and pushed to the distal end portion 42 of the probe-receiving tube 36 through the open proximal end 48, supported by an encapsulated cable 72 of conventional form. The cable 72 is preferably of a type which is able to reorient the transducer probe 70 controllably to transmit ultrasound vibrations in various required directions, as illustrated by the position of the transducer probe 70 shown in broken line in FIG. 3. Additionally, the cable 72 and the ultrasound transducer probe 70 may be rotated within the probe-receiving tube, about the longitudinal axis 74 of the cable 72, to obtain an ultra-sound image in a desired direction.

To assure good acoustic coupling, particularly where the transducer 70 may not be in intimate contact with the interior surface 63 of the probe-receiving tube 36, a quantity of a liquid acoustic coupling medium, such as water, may be introduced into the extension tube 54 through the end coupling 58, to displace air surrounding the transducer probe 70 within the interior space 64.

When the probe 70 and its cable 72 are not located within the interior space 64, the distal portion 48 of the probe-receiving tube 36 is free to collapse under the forces of its own elasticity and the pressures encountered within the body cavity where the probe-receiving tube is located, to the configuration shown in FIG. 6.

While the invention has been described above in connection with preferred embodiments, it will be understood that the probe-receiving tube 36 of the invention may be unsupported or may be supported by an elongate support member of a different construction and can he utilized for repeated temporary insertion and removal of a medical sensor such as an ultrasound transducer probe in different internal cavities of the body of a patient 12 either briefly or over an extended time of as much as several days. The probe-receiving tube of the invention thus can be used in order to scan organs within the patient's body with ultrasound or provide ultrasound transmissions for purposes of obtaining Doppler measurements, either through an opening such as the surgical opening 14, or through a natural orifice of the patient's body, such as the trachea, urethra and bladder, or rectum, so that ultrasound wave or other signal propagation to and from the organ is more direct than when transmitted through the patient's skin and layers of external tissue or bones.

The terms and expressions which have been employed in the foregoing specification are used therein as terms of description and not of limitation, and there is not intention, in the use of such terms and expressions, of excluding equivalents of the features shown and described or portions thereof, it being recognized that the scope of the invention is defined and limited only by the claims which follow.

What is claimed is:

1. A device for use in a medical procedure for placing a sensor probe temporarily in a desired location within a patient's body, comprising:
   (a) an elongate support member having a distal end portion and a proximal portion, at least said distal end portion being manually deformable to be given and to retain a desired revised shape; and
   (b) a thin-walled probe-receiving tube of flexible material attached to and extending along said distal end portion of said support member, said tube having a closed distal end defining an interior space within said tube.

2. The device of claim 1 wherein said probe-receiving tube includes a coating of a friction-inhibiting material on an inner surface.

3. The device of claim 1 wherein said distal end portion of said support member is detachable from said probe-receiving tube in a zone extending along said tube for a predetermined distance from said closed distal end of said probe-receiving tube.

4. The device of claim 1 wherein said revised shape includes an angular diversion from an original axial direction of said support member.

5. The device of any of claim 1, 2, 3, or 4, wherein said elongate support member is a chest drain tube.

6. The device of claim 5 including a plurality of said drain tubes each including a respective distal portion that is separately detachable from said probe-receiving tube and deformable to be given and to retain a respective revised shape.

7. A device for use in a medical procedure for placing a sensor probe temporarily in a desired location within a patient's body, comprising:
   (a) an elongate support member having a distal end portion, an intermediate portion, and a proximal portion; and
   (b) a thin-walled probe-receiving tube of flexible material attached to and extending closely alongside said intermediate portion of said support member, said tube having a closed distal end defining an interior space within said tube, said closed distal end and an adjacent distal end portion of said probe-receiving tube being detached and free from said support member.

8. The device of claim 7 wherein said closed distal end and said adjacent distal end portion of said probe-receiving tube have a combined length in the range of 5 to 15 cm.

9. A device for use in a medical procedure for placing a sensor probe temporarily in a desired location within a patient's body, comprising:
   (a) an elongate support member having a distal end portion and a proximal portion; and
   (b) a thin-walled probe-receiving tube of flexible material integral with and extending closely alongside said distal end portion of said support member, said thin-walled probe-receiving tube having a closed distal end defining an interior space within said tube and said elongate support member being a drain tube including an opening for draining material from said location within said patient's body, said drain tube having a thin wall which is substantially more difficult to collapse than said thin-walled probe-receiving tube.

10. The device of claim 9 wherein said wall of said drain tube is of generally circular cross-sectional shape and is of flexible material and has a reinforcing structure embedded therein.

11. The device of claim 10 wherein said embedded reinforcing structure is a wire in the form of a helix extending along and surrounding an interior lumen of said drain tube.

12. The device of claim 11 wherein said wire is of malleable metal.

13. The device of claim 10 including a malleable wire extending longitudinally of said drain tube and embedded in said wall thereof.

14. A device for use in a medical procedure for placing a sensor probe temporarily in a desired location within a patient's body, comprising:
   (a) an elongate support member having a distal end portion and a proximal portion; and
   (b) a probe-receiving tube having a thin wall of flexible material, said probe-receiving tube extending closely alongside and being securely attached to said distal end portion of said support member, said probe-receiving tube having a closed distal end defining an interior space within said probe-receiving tube, and said device including a portion adjacent said closed distal end of said probe-receiving tube that is relatively opaque to ultrasound waves.

15. The device of claim 14 wherein said support member is a drain tube including a plurality of distal end portions, each defining a respective lumen and said respective lumens communicating with each other.

16. The device of claim 15 wherein at least one of said plurality of distal end portions of said drain tube includes a formable support member holding said at least one of said distal end portions in a desired configuration.

17. The device of claim 16 wherein said distal end portions of said drain tube converge and join each other in a single proximal drain tube outlet portion.

* * * * *